United States Patent [19]

Ushiro

[11] 4,343,902
[45] * Aug. 10, 1982

[54] PRODUCTION OF IMMOBILIZED GLUCOSE ISOMERASE

[75] Inventor: Soichiro Ushiro, Kokubunji, Japan

[73] Assignee: CPC International Inc., Englewood Cliffs, N.J.

[*] Notice: The portion of the term of this patent subsequent to Apr. 21, 1998, has been disclaimed.

[21] Appl. No.: 217,976

[22] Filed: Dec. 19, 1980

[30] Foreign Application Priority Data

Feb. 5, 1980 [JP] Japan .................................. 55-12111

[51] Int. Cl.$^3$ ..................... C12N 11/02; C12P 19/24; C12N 9/92
[52] U.S. Cl. ...................................... 435/177; 435/94; 435/180; 435/234; 435/259; 435/815
[58] Field of Search ................. 435/94, 174, 177, 180, 435/234, 814, 815, 259

[56] References Cited

U.S. PATENT DOCUMENTS

| | | | |
|---|---|---|---|
| 3,948,728 | 4/1976 | Roeschlau et al. | 435/814 X |
| 4,113,568 | 9/1978 | Fujita et al. | 435/94 X |
| 4,144,129 | 3/1979 | Gruber et al. | 435/814 X |
| 4,263,400 | 4/1981 | Ushiro | 435/177 |

FOREIGN PATENT DOCUMENTS 1411503 10/1975 United Kingdom ................ 435/259

*Primary Examiner*—David M. Naff

[57] ABSTRACT

An immobilized glucose isomerase is prepared by treating an aqueous suspension of cells of a glucose isomerase producing microorganism with a non-ionic surfactant that solubilizes glucose isomerase contained by the cells without solubilizing polysaccharides in the cells, separating the cells from the aqueous suspension, and adsorbing glucose isomerase from the resultant solution onto an ion exchange resin. By this process, contaminating polysaccharides are eliminated that inhibit adsorption of glucose isomerase on the ion exchange resin.

4 Claims, No Drawings

PRODUCTION OF IMMOBILIZED GLUCOSE ISOMERASE

BACKGROUND OF THE INVENTION

1. Field of the Invention

The present invention relates to immobilized enzymes and particularly relates to immobilized glucose isomerase and methods of producing same.

2. The Prior Art

The term 'glucose isomerase' is the generic name used for those enzymes which transform glucose to fructose, and their main application lies in the production of fructose from glucose. That is, glucose isomerases are currently employed industrially for the production of fructose-containing syrups by isomerization of glucose. This reaction has conventionally been carried out by the batch method, with a solution containing a high concentration of glucose being contacted with a glucose isomerase for about 48 hours at a temperature of 60° to 70° C. However, since this reaction is performed in batches, there have been problems such as a poor utilization rate of the glucose isomerase, discoloration of the product due to the reaction being carried out for extended periods at high temperature, high costs for refining the product following the reaction, and so on.

In addition, in recent years industrial applications of continuous isomerization methods have been developed using immobilized glucose isomerases prepared by adsorbing or binding a glucose isomerase on a special carriers, for example, an ion exchange resin or DEAE-cellulose.

Glucose isomerases are generally produced inside the cells of microorganisms. That is to say, most of the produced glucose isomerase exists inside the cell wall or on the cell wall of the producing microorganism. For this reason, in order to carry out adsorption of a glucose isomerase on a carrier such as an ion exchange resin, the glucose isomerase must first be separated from the cells of the microorganism and employed in the form of a solution. Some examples of methods employing glucose isomerase in this way in the form of a solution are disclosed in U.S. Pat. Nos. 3,708,397; 3,788,945; 3,850,751 and 3,868,304. However, when following these methods for achieving adsorption of glucose isomerase on a carrier such as an ion exchange resin, there are various problems encountered such as a low level of adsorption of the glucose isomerase on the ion exchange resin or other carrier, and this results in the obtained immobilized glucose isomerase having a low isomerizing efficiency in the continuous isomerization system.

It has now been found, in accordance with the present invention, that a polysaccharide which is contained in the abovementioned solutions of glucose isomerase is competitively or preferentially adsorbed on the ion exchange resin or other carrier, and this adsorption of polysaccharide acts to inhibit the adsorption of the glucose isomerase itself on the ion exchange resin or other kind of carrier. That is, it was found that an adsorbed polysaccharide makes it difficult to immobilize glucose isomerases on carriers such as ion exchange resins. For this reason the glucose isomerase adsorbed on the ion exchange resin or other carrier is low. It should be understood in this context that "polysaccharides" means higher molecular weight saccharides which are not released into the dialysate and are retained in the glucose isomerase solution when said glucose isomerase solution is dialysed for one night against deionized water containing 10 mM $MgCl_2$ and 1 mM $CoCl_2$.

Further, in accordance with the present invention, it has been discovered that it is possible to adsorb a large amount of glucose isomerase on a carrier such as an ion exchange resin employed for the immobilization of said glucose isomerase if said contaminating polysaccharide is first eliminated from the cultured material obtained by culturing a microorganism producing glucose isomerase. It has also been found that it is possible to achieve an elevated efficiency in the isomerization reaction when the immobilized glucose isomerase obtained in this way is employed in a continuous isomerization system. Based on this finding, the present inventor obtained U.S. Pat. No. 4,263,400 on Apr. 21, 1981. The present invention is a result of further studies on the removal of the polysaccharide from the cultured material of the glucose isomerase producing microorganisms.

SUMMARY OF THE INVENTION

This invention relates to a method for the production of immobilized glucose isomerase comprising adding a non-ionic surfactant to a cultured material obtained by culturing a glucose isomerase producing microorganism or moist cells obtained therefrom, or an aqueous suspension thereof. The cultured material, the moist cells or the aqueous suspension of cells is then autolysed in order to solubilize the glucose isomerase without solubilizing the polysaccharides present and thereby obtain a glucose isomerase solution containing no or almost no polysaccharide. Said glucose isomerase solution is then contacted with a carrier which is capable of adsorbing glucose isomerase and the glucose isomerase is adsorbed on said carrier.

DETAILED DESCRIPTION OF THE INVENTION

With respect to the cultured material obtained by culturing a glucose isomerase producing microorganism, it is possible to use any cultured material obtained by culturing a glucose isomerase producing microorganism. For example, it is possible to use a cultured material obtained by culturing an actinomycetes such as *Streptomyces olivochromogenes,* or a bacterium such as *Lactobacillus brevis* or *Bacillus coagulans.*

The cultured material is autolysed by direct addition of a non-ionic surfactant thereto or, it is also possible to carry out autolysis by adding a non-ionic surfactant to an aqueous suspension of the moist cells obtained by an appropriate means such as centrifugation from the cultured material. The surfactant is a surface active substance having both hydrophilic and hydrophobic groups in its molecular structure and is used for interfacial adjustment. Examples of commercially available surfactants for the autolysis are TRITON (manufactured by Sigma Co., U.S.A.), BRIJI (manufactured by Kao Atlas, Japan) or TWEEN (manufactured by Tokyo Kasei Kogyo Co., Japan). It is also possible to use any non-ionic surfactant which will solubilize the glucose isomerase without solubilizing the polysaccharides present in the cells.

An appropriate addition level for the non-ionic surfactant is between 0.1 and 20%, preferably 0.5 to 5% relative to the weight of the dried cells.

After adjusting the pH to 5 to 8, preferably 5.5 to 7.5, the cultured material, the moist cells or its aqueous suspension is autolysed at 30° C. to 70° C., preferably at 45° C. to 60° C., for 8 to 24 hours, preferably 10 to 15 hours, while stirring. The autolysis thus conducted results in a solution containing solubilized glucose isomerase, but which contains no or almost no polysaccharide. This can be demonstrated by analyzing the solution using the phenol sulfuric acid method after dialysis.

The autolysate thus obtained is preferably cooled down to room temperature and the solid fraction is removed by an appropriate means such as filtration or centrifugation. Prior to the solid separation, it is effective to add an organic solvent, for example, methanol, ethanol, propanol, isopropanol, acetone, t-butanol or p-dioxane, with isopropanol being especially desirable.

The addition of the organic solvent should be made to the extent that no precipitation of glucose isomerase takes place. For example, in the case of isopropanol, the addition level should be 30 to 45%, preferably 36 to 40% relative to the above autolysate. It is also possible to add the organic solvent prior to the termination of the autolysis. In this case, the temperature for the autolysis should be selected so as not to volatilize the organic solvent. A glucose isomerase solution which contains no or almost no polysaccharide is thus obtained.

Concerning the carrying out the adsorption of the glucose isomerase solution thus obtained, if the solution does not contain any organic solvent, it is possible to use the solution as it is. However, when an organic solvent is added to the solution, the glucose isomerase is precipitated out first by an appropriate method, for example, adding magnesium chloride or magnesium sulfate to the solution to a concentration of 10 to 200 mM, preferably 40 to 60 mM. Then the supernatant is removed, for example, by centrifugation, and the glucose isomerase precipitate is dissolved in ion-exchange water. A glucose isomerase solution containing no or almost no polysaccharide is thus obtained.

The glucose isomerase containing solution, which is obtained in the above-mentioned way and which has been completely or nearly completely purified with respect to polysaccharide, is then contacted with a glucose isomerase adsorbing carrier and the glucose isomerase is adsorbed thereon.

Suitable glucose isomerase adsorbing carriers are, for example, glucose isomerase adsorbing ion exchange resins, DEAE-cellulose, basic magnesium carbonate, colloidal silica, active carbon, and Controlled Pore Alumina.

Exemplary glucose isomers adsorbing ion exchange resins are Amberlite IRA-904, Amberlite IRA-938, Amberlite IRA-93 (the foregoing are all brand names of products of Tokyo Yuki Kagaku Kogyo Co., Ltd.), Duolite A-2, Duolite A-7, Duolite 5-30, Duolite ES-561, Duolite ES-562 and Duolite ES-568 (the foregoing are all brand names of products of Diamond Shamrock Chemical Co., Ltd., of the U.S.A.).

Examples of DEAE-cellulose are Selectacel-20 (the brand name of a product of Braun Co., of West Germany). Suitable colloidal silicas are LUDOX HS-30, LUDOX HS-40, LUDOX AM, LUDOX TM (all of the foregoing are brand names of products of DuPont Co., Ltd., of the U.S.A.), Snowtex 20, Snowtex 30 and Snowtex N (all of the the foregoing are brand names of products of Nissan Kagaku Co., Ltd.).

Controlled Pore Alumina is available from Corning Co., Ltd.

Suitable active carbons include Darco S-51 and Darco G60 (both brand names of products of Atlas Co., Ltd., of Denmark).

At the time of carrying out the adsorption of the glucose isomerase by contacting a glucose isomerase containing solution which contains no or almost no polysaccharide with one of the above-mentioned glucose isomerase adsorbing carriers, said glucose isomerase solution, either as it is or after it has been adjusted to a suitable concentration (a glucose isomerase concentration of 50/ml to 1,000 U/ml, preferably about 300 U/ml) by concentration or dilution, is contacted with the carrier. This can be done in a column or in some other appropriate vessel. For purposes of this specification, one unit of enzyme activity is defined as the amount of enzyme which forms 1 $\mu$M fructose in one minute when incubated with a 0.1 M glucose solution in the presence of 0.01 M $MgCl_2$ and 0.001 M $CoCl_2$.

When the carrier is an ion exchange resin, it is possible for the exchange group to be any of OH-form, Cl-form, $SO_4$ form, etc., but it is most desirable to employ the Cl- form derived from NaCl or HCl.

Moreover, at the time of adsorption of glucose isomerase to the above-mentioned carriers, it is desirable for the pH of the glucose isomerase containing solution to be in the range of 4 to 11, especially in the range of about pH 7 to 8. In addition, the temperature at the time of adsorption of the glucose isomerase should be between 4° C. and 60° C., especially at about room temperature.

When the glucose isomerase adsorption is done in a column, the above-mentioned glucose isomerase containing solution should be introduced to said column at a flow-rate of SV 0.5 to SV 10 (SV means Space Velocity which indicates the hourly amount of solution passed through the column in terms of the proportion to the bed volume of the column) and preferably at SV 1.0. Alternatively, the adsorption can be carried out by circulating said glucose isomerase containing solution through the column for a period of 3 hours to 24 hours, preferably for a period of 10 hours to 15 hours.

When the glucose isomerase adsorption is done in a suitable vessel as a batch-type adsorption, the above-mentioned glucose isomerase containing solution should be contacted with the above-mentioned carriers for a period of 30 minutes to 24 hours, preferably for a period between 2 hours and 5 hours, while stirring the mixture, and thus the glucose isomerase will be adsorbed on the selected carrier.

Therefore, by following the above procedure for contacting a glucose isomerase containing solution which contains no or almost no polysaccharide with a glucose isomerase adsorbing carrier and adsorbing said enzyme thereto, an immobilized glucose isomerase is obtained.

Pursuant to the present invention, therefore, by employing a glucose isomerase solution which are obtained through a selective separation of the polysaccharide fraction from cultured material of a glucose isomerase producing microorganism, one can readily obtain an immobilized glucose isomerase which has a very high adsorption efficiency in relation to glucose isomerase adsorbing carriers and which is capable of carrying out continuous glucose isomerase isomerization reactions at extremely high efficiency. As a result of this, it is possible to greatly reduce both the cost of production of immobilized glucose isomerase and the cost of the enzyme employed in the isomerization reaction.

The following examples are given to illustrate further the present invention.

EXAMPLE 1

A glucose isomerase producing microorganism, *Streptomyces olivochromogenes (FERM P 1640, ATCC 21,114)* was cultured in a liquid medium (xylose 2%, corn starch 4%, CSL 4%, glycine 0.1%, ammonimum nitrate 0.2%, magnesium sulfate $7H_2O$ 0.05%) at 30° C. for about 50 hours with shaking. The microbial cells are collected from the cultured material by centrifugation at 10,000 rpm for 20 minutes. After homogenizing the collected cells in a mixer, 2700 g of moist cells were obtained. The moisture content of the moist cells was determined by lyophilizing a portion of the moist cells and weighing the dried cells. It was found to be 80%. A portion of the moist cells was also disintegrated by sonication and the glucose isomerase activity was determined. It was found that the activity was 384 units per gram of moist cells.

Two hundred and fifty grams of the moist cells (50 g of dried cells, containing 96,000 units of glucose isomerase activity) were placed in a 2-liter flask and were suspended in ion-exchange water. TRITON X-100 (500 mg, manufactured by Sigma Co., U.S.A.) was added to this at a level of 1% per gram of dried cells, the pH was adjusted to 6.0 with 1 N·$CH_3COOH$, and the total amount was made up to 1,000 g with an ion-exchange water. This cell suspension was autolysed at 50° C. for 12 hours while stirring at 200 rpm. After cooling the autolysate thus obtained to room temperature, 582 g of cold isopropanol was added while stirring gently. This mixture was filtered through Celite 535 (manufactured by Junsei Chemical Co.), a filtering aid, using an aspirator and the residual cells were washed well with about 200 g of a 38 W/W % isopropanol solution.

The filtrate and the wash were combined (1,700 g). This was referred to as glucose isomerase Solution A.

As a result of the determination of the glucose isomerase activity in Solution A it was found that 95,600 units of glucose isomerase was solubilized, which corresponds to 99.6% of the total glucose isomerase activity in the cells used for solubilization.

Next, 1,700 g of this glucose isomerase Solution A was introduced to a 2 liter beaker and 17 g of $MgCl_2.6H_2O$ was added to it while stirring; the stirring was continued for 1 hour at room temperature.

After centrifuging this solution at 15,000 rpm for 15 minutes, the supernatant was discarded by decantation and the precipitate was dissolved in about 30 ml of ion-exchange water. Thus, 43.2 g of a refined glucose isomerase solution, designated Solution P, was obtained.

As a result of determination of the glucose isomerase activity and total saccharide content measured by the phenol sulfuric acid method, it was found that Solution P contained 93,890 units of glucose isomerase activity. This was 97.8% of the total glucose isomerase activity of the cells subjected to solubilization and 2.03 gamma of total saccharide content per unit GI activity.

Then, 4.6 g of glucose isomerase Solution P (containing 9,998 units of GI) was introduced to a 2.2×20 cm column packed with 20 ml of moist Amerberlite IRA-904 (carrier) and circulated through the column overnight at SV 1 and room temperature.

As a result, 100% of the supplied glucose isomerase was adsorbed on the carrier.

EXAMPLE 2

Two hundred and fifty grams of moist cells (50 g dried cells; 96,000 units of GI), prepared in accordance with the procedure described in Example 1, was placed in a 2 liter flask and suspended in 700 g of ion-exchange water. TWEEN 60 (500 mg. manufactured by Tokyo Kasei Kogyo Co.) was added to the cell suspension at 1% relative to the dry cell weight, then the pH was adjusted to 6.0 with 2 N $CH_3COOH$ and the total amount was made up to 1,000 g with ion-exchange water. This cell suspension was autolysed at 50° C. for 12 hours while stirring at 200 rpm. After cooling the autolysate solution thus obtained to room temperature, 582 g of cold isopropanol was added while stirring gently. This mixture was filtered through Celite 535 as a filtering aid using an aspirator and the residual cells were washed well with about 200 g of a 38 W/W % isopropanol solution. The filtrate and the wash were combined (1700 g) and this was referred to as glucose isomerase Solution B.

As a result of determination of the glucose isomerase activity in Solution B, it was found that 94,850 units of glucose isomerase was solubilized, which corresponds to 98.8% of the total glucose isomerase activity in the cells subjected to solubilization.

Then 1,700 g of glucose isomerase Solution B was introduced to a 2 liter beaker and 17 g of $MgCl_2.6H_2O$ was added to it while stirring; stirring was continued for 1 hour at room temperature. After centrifuging this solution at 15,000 rpm for 15 minutes, the supernatant was discarded by decantation and the precipitate was dissolved in about 30 ml of ion-exchange water. Thus, 44.1 g of a refined glucose isomerase, Solution Q, was obtained.

As a result of determination of the glucose isomerase activity and total saccharide content, it was found that Solution Q contained 93,410 units of glucose isomerase activity, which was 97.3% of the total glucose isomerase activity in the cells subjected to solubilization, and 2.18 gamma of total saccharide content per unit GI activity.

Next, 4.72 g of this glucose isomerase Solution Q (containing 9,998 units of GI) was introduced to a 2.2×20 cm column packed with 20 ml of moist Amberlite IRA-904 (carrier) and circulated through the column overnight at SV 1 and room temperature.

As a result, 100% of the supplied glucose isomerase was adsorbed on the carrier.

EXAMPLE 3

Two hundred and fifty grams of moist cells (50 g dried cells, 96,000 units GI), prepared in accordance with the procedure described in Example 1, was placed in a 2 liter flask and suspended in 700 g of ion-exchange water. BRIJI 35 (500 mg, manufactured by Kao Atlas) was added to the cell suspension at a level of 1% relative to the weight of the dried cells, the pH was adjusted to 6.0 with 1 N $CH_3COOH$, and the total amount was made up to 1,000 g with ion-exchange water. This cell suspension was autolysed at 50° C. for 12 hours while stirring at 200 rpm. After cooling the autolysate solution thus obtained to room temperature, 582 g of cold isopropanol was added while stirring gently.

This mixture was filtered through Celite 535 as a filtering aid using an aspirator and the residual cells were washed well with about 200 g of a 38 W/W % isopropanol solution. The filtrate and the wash were combined (1,700 g) and this was referred to as glucose isomerase Solution C. As a result of determination of the glucose isomerase activity in this Solution C, it was found that 93,600 units of glucose isomerase was solubilized; this corresponds to 97.5% of the total glucose isomerase activity in the cells subjected to the solubilization.

Next, 1,700 g of glucose isomerase Solution C was introduced to a 2 liter beaker and 17 g of $MgCl_2.6H_2O$ was added while stirring; stirring was continued for 1 hour at room temperature. After centifuging this solution at 15,000 rpm for 15 minutes, the supernatant was discarded by decantation and the precipitate was dissolved in about 30 ml of ion-exchange water. Thus, 45.3 g of refined glucose isomerase Solution R was obtained.

As a result of determination of the glucose isomerase activity and total saccharide content, it was found that Solution R contained 93,210 units of glucose isomerase activity, which was 97.1% of the total glucose isomerase activity in the cells subjected to solubilization, and 2.35 gamma of total saccharide content per unit GI activity.

Next, 4.86 g of this glucose isomerase Solution R (containing 10,000 units GI) was introduced to a 2.2×20 cm column packed with 20 ml of a moist Amberlite IRA-904 (carrier) and circulated through the column overnight at SV 1 and room temperature.

As a result, 100% of the supplied glucose isomerase was adsorbed on the carrier.

Comparative Example

Two hundred and fifty grams of moist cells (50 g dried cells, 96,000 units GI), prepared in accordance with the procedure described in Example 1, was placed in a 2 liter flask and suspended in 700 g of ion-exchange water. The pH was adjusted to 6.0 with 1 N $CH_3COOH$. To this cell suspension, 0.05% lysozyme/gm dry cell weight (25 mg, manufactured by Boehringer Mannheim) was added and the total amount was made up to 1,000 g with ion-exchange water. This cell suspension was lysed at 50° C. for 12 hours while stirring at 200 rpm. After cooling the autolysate thus obtained to room temperature, 582 g of cold isopropanol was added while stirring gently. This mixture was filtered through Celite 535 as a filtering aid using an aspirator, and the residual cells were washed well with about 200 g of a 38 W/W % isopropanol solution. The filtrate and the wash wire combined and this was referred to as glucose isomerase Solution D. As a result of determination of the glucose isomerase activity in Solution D, it was found that 93,980 units of glucose isomerase was solubilized, which corresponds to 97.9% of the total glucose isomerase activity in the cells subjected to the solubilization.

Next, 1,700 g of this glucose isomerase Solution D was introduced to a 2 liter beaker and 17 g of $MgCl_2.6H_2O$ was added to it while stirring; stirring was continued for 1 hour at room temperature. After centrifuging this solution at 15,000 rpm for 15 minutes, the supernatant was discarded by decantation and the precipitate was dissolved in about 30 ml of ion-exchange water. Thus, 44.7 g of refined glucose Solution S was obtained.

As a result of determination of the glucose isomerase activity and total saccharide content, it was found that Solution S contained 92,930 units of glucose isomerase activity, which was 96.8% of the total glucose isomerase activity in the cells subjected to the solubilization, and 8.38 gamma of total saccharide content per unit GI activity. As shown above, the total saccharide content of this solution was remarkably higher than those of the solutions prepared according to the invented process.

Then 4.81 g of the glucose isomerase solution (containing 10,000 units GI) was introduced to a 2.2×20 cm column packed with 20 ml of moist Amberlite IRA-904 (carrier) and circulated through the column overnight at SV 1 and room temperature.

As a result, 61.8% of the supplied glucose isomerase was adsorbed on the carrier.

Having set forth the general nature and some specific examples of the present invention, the scope is now particularly set forth in the appended claims.

What is claimed is:

1. A method for the production of immobilized glucose isomerase comprising:
    (a) culturing a glucose-isomerase producing microorganism in a suitable medium to produce cells of the microorganism;
    (b) treating an aqueous suspension of the cells of said microorganism at a pH of from about 5 to about 8 and at a temperature from about 30° C. to about 70° C. with from about 0.1% to about 20% by weight, based on the dry weight of the cells, of a non-ionic surfactant that solubilizes the glucose isomerase without solubilizing the polysaccharides in the cells, for a sufficient time to solubilize the glucose isomerase and give a glucose isomerase solution;
    (c) separating the glucose isomerase solution from the cells; and
    (d) adsorbing the glucose isomerase from said glucose isomerase solution on an ion exchange resin capable of adsorbing said polysaccharides.

2. The process of claim 1 wherein the cells are treated with from about 0.5 to about 5% by weight, based on the dry weight of the cells, of a non-ionic surfactant.

3. The process of claim 1 wherein the microorganism is obtained from a Streptomyces microorganism.

4. The process of claim 3 wherein the microorganism is a strain of *Streptomyces olivochromogenes*.

* * * * *

UNITED STATES PATENT AND TRADEMARK OFFICE
CERTIFICATE OF CORRECTION

PATENT NO. : 4,343,902
DATED : August 10, 1982
INVENTOR(S) : Soichiro Ushiro

It is certified that error appears in the above-identified patent and that said Letters Patent are hereby corrected as shown below:

Column 1, line 31, delete "carriers" and insert --carrier--.
Column 1, line 54, delete "abovementioned" and insert --above-mentioned--.
Column 3, line 25, after "out" insert --of--.
Column 3, line 50, delete "isomers" and insert --isomerase--.
Column 4, line 57, delete "are" and insert --was--.
Column 5, line 10, delete "are" and insert --were--.
Column 7, line 50, delete "wire" and insert --were--.

Signed and Sealed this

Fifth Day of July 1983

[SEAL]

Attest:

GERALD J. MOSSINGHOFF

Attesting Officer    Commissioner of Patents and Trademarks